United States Patent
Prakash et al.

(10) Patent No.: US 6,627,431 B1
(45) Date of Patent: Sep. 30, 2003

(54) CHEMOENZYMATIC SYNTHESIS OF NEOTAME

(75) Inventors: Indra Prakash, Hoffman Estates, IL (US); Robert Y. Zhao, Mount Prospect, IL (US)

(73) Assignee: The NutraSweet Company, Chicago, IL (US)

( * ) Notice: Subject to any disclaimer, the term of this patent is extended or adjusted under 35 U.S.C. 154(b) by 0 days.

(21) Appl. No.: 09/570,408

(22) Filed: May 12, 2000

(51) Int. Cl.$^7$ .................................................. C07C 1/00
(52) U.S. Cl. ...................... 435/280; 435/183; 435/135; 435/134; 560/40
(58) Field of Search ................................ 435/280, 183, 435/135, 134; 560/40

(56) References Cited

U.S. PATENT DOCUMENTS

| | | | |
|---|---|---|---|
| 3,933,781 A | 1/1976 | Bachman et al. | 260/112.5 |
| 4,293,648 A | 10/1981 | Davino | 435/70 |
| 5,480,668 A | 1/1996 | Nofre et al. | 426/548 |
| 5,510,508 A | 4/1996 | Claude et al. | 560/41 |
| 5,728,862 A | 3/1998 | Prakash | 560/40 |
| 5,928,909 A | * 7/1999 | Prakash | 435/106 |
| 6,077,962 A | * 6/2000 | Prakash | 549/253 |

FOREIGN PATENT DOCUMENTS

| | | |
|---|---|---|
| JP | 62-74297 | 4/1987 |
| WO | 98/08968 | 3/1998 |
| WO | 00/32622 | 6/2000 |
| WO | 00/39075 | 7/2000 |

OTHER PUBLICATIONS

C. Nofre, et al., "Neotame: Discovery, Properties, Utility", Food Chem., vol. 69, pp. 245–257 (2000).
A. Pandey, et al., "The Realm of Microbial Lipases in Biotechnology", Biotechnol. Appl. Biochem., vol. 29, pp. 119–131 (1999).
K. Jaeger, et al., "Microbial Lipases Form Versatile Tools for Biotechnology", TIBTECH, vol. 16, pp. 396–403 (1998).
E. Guibe–Jampel, et al., "Enantioselective Hydrolysis of Racemic Diesters by Porcine Pancreatic Lipase", J. Chem. Soc., Chem. Commun., pp. 1080–1081 (1987).
K.A. Stein, et al., "Enzyme–Catalyzed Regioselective Hydrolysis of Aspartate Diesters", J. Org. Chem., vol. 60, pp. 8110–8112 (1995).
M. Adamczyk, et al., "Lipase Mediated Hydrolysis of Rapamycin 42–Hemisuccinate Benzyl and Methyl Esters", Tetrahedron Lett., vol. 35, No. 7, pp. 1019–1022 (1994).
L.T. Kanerva, et al., "Approach to Highly Enantiopure β–Amino Acid Esters by Using Lipase Catalysts in Organic Media", Tetrahedron: Assymetry, vol. 7, No. 6, pp. 1705–1716 (1996).

\* cited by examiner

*Primary Examiner*—Irene Marx
(74) *Attorney, Agent, or Firm*—Fitzpatrick, Cella, Harper & Scinto

(57) ABSTRACT

A chemoenzymatic method is disclosed for preparing N-[N-(3,3-dimethylbutyl)-L-α-aspartyl]-L-phenylalanine 1-methyl ester via the enzymatic regioselective hydrolysis of neotame esters using lipases or esterases.

7 Claims, 4 Drawing Sheets

CHEMOENZYMATIC SYNTHESIS OF NEOTAME

BACKGROUND OF THE INVENTION

1. Field of the Invention

This invention relates to the chemoenzymatic synthesis of neotame (N-[N-(3,3-dimethylbutyl)-L-α-aspartyl]-L-phenylalanine 1-methyl ester) via regioselective hydrolysis of neotame esters. Neotame is particularly useful as a sweetening agent.

2. Related Background Art

N-[N-(3,3-dimethylbutyl)-L-α-aspartyl]-L-phenylalanine 1-methyl ester is a derivative of aspartame that has a sweetening potency that is about 40 times that of aspartame (and about 8,000 times that of sucrose). N-[N-(3,3-dimethylbutyl)-L-α-aspartyl]-L-phenylalanine 1-methyl ester may be prepared from aspartame as described in U.S. Pat. No. 5,480,668, U.S. Pat. No. 5,510,508, and U.S. Pat. No. 5,728,862, all of which are incorporated by reference herein.

These patents describe methods for preparing neotame by treating a mixture of aspartame and 3,3-dimethylbutyraldehyde with reducing agents. There is a need, however, to develop more cost-effective and efficient methods of preparing high purity neotame from readily obtainable materials.

Neotame may be used for sweetening a variety of products, including drinks, foods, confectionery, pastries, chewing gums, personal care, hygiene products and toiletries, as well as cosmetic, pharmaceutical and veterinary products. Its superior sweetening potency makes neotame an attractive alternative to aspartame because it permits the use of neotame in substantially smaller quantities than is required for aspartame to achieve an equivalent sweetening effect.

Enzymes are becoming increasingly important as catalysts for asymmetric synthesis. Of particular importance are the hydrolytic enzymes, namely hydrolases. There are many examples of the synthetic utility of hydrolases, and there are many commercially available sources from which to obtain such enzymes. Lipases and esterases are widely used for ester hydrolysis, transesterification, acetylation and diastereomeric separation. Lipase and esterase catalyzed regioselective transesterification and de-esterification have been shown to be excellent alternatives to traditional esterification and de-esterification. U.S. Pat. No. 5,928,909 disclosed regioselective and chemoselective hydrolysis of an α-ester group of an amino acid diester using pig liver esterase. Porcine pancreatic lipases and lipases from *Candida rugosa* and Pseudomonas sp. were used for enantioseletive transesterification in organic synthesis. Liisa Kanerva, et al. (*Tetrahedron: Asymmetry*, 7(6): 1705–1716, 1996), synthesized highly enantiopure β-amino acid esters using catalysis lipases from *Candida antarctica* and *Pseudomonas cepacia*. Adamczky et al. (*Tetrahedron Lett.*, 35(7): 1019–22, 1994.) used lipases from Pseudomonas species to mediate hydrolysis of rapamycin 42-hemisuccinate benzyl and methyl esters. Stein et al. (*J. Org. Chem.*, 60: 8110, 1995.) demonstrated that the hydrolysis of aspartate dimethyl ester using pig liver esterase resulted in the hydrolysis of both ester groups, i.e. the α-ester group and the β-ester group. The selectivity of the α-ester hydrolysis to the β-ester hydrolysis was found to be 98:2 for the formation of the corresponding aspartate monoesters. In contrast, both the (R)-aspartate diethyl ester and (S)-aspartate diallyl ester are converted to their respective β-monoesters with pig liver esterase with complete regioselectivity hydrolysis of the a-ester group (U.S. Pat. No. 5,928,909). In addition, it was found that the preferential hydrolysis for the α-ester position is found to be partially reversed when the aspartate is N-protected as its formamide. The selectivity for the N-protected aspartame was found to be 55:45 for the α-ester hydrolysis to the β-ester hydrolysis. Guibe-Jampel et al. (*J. Chem. Soc., Chem. Commun.*, 1080, 1987) used porcine pancreatic lipase (PPL) for regioselective hydrolysis of dialkyl amino acid esters. Hydrolysis of N-protected dialkyl aspartates using PPL resulted in the regioselective hydrolysis of the β-ester group and formation of the corresponding N-protected α-ester aspartate. However, in the case of N-alkylated aspartate ester which conjugated with phenylalanine ester, regioselective hydrolysis with hydrolases was not reported.

SUMMARY OF THE INVENTION

This invention relates to the chemoenzymatic synthesis of neotame (N-[N-(3,3-dimethylbutyl)-L-α-aspartyl]-L-phenylalanine 1-methyl ester) via regioselective hydrolysis of neotame esters.

DETAILED DESCRIPTION OF THE INVENTION

Figure 1:
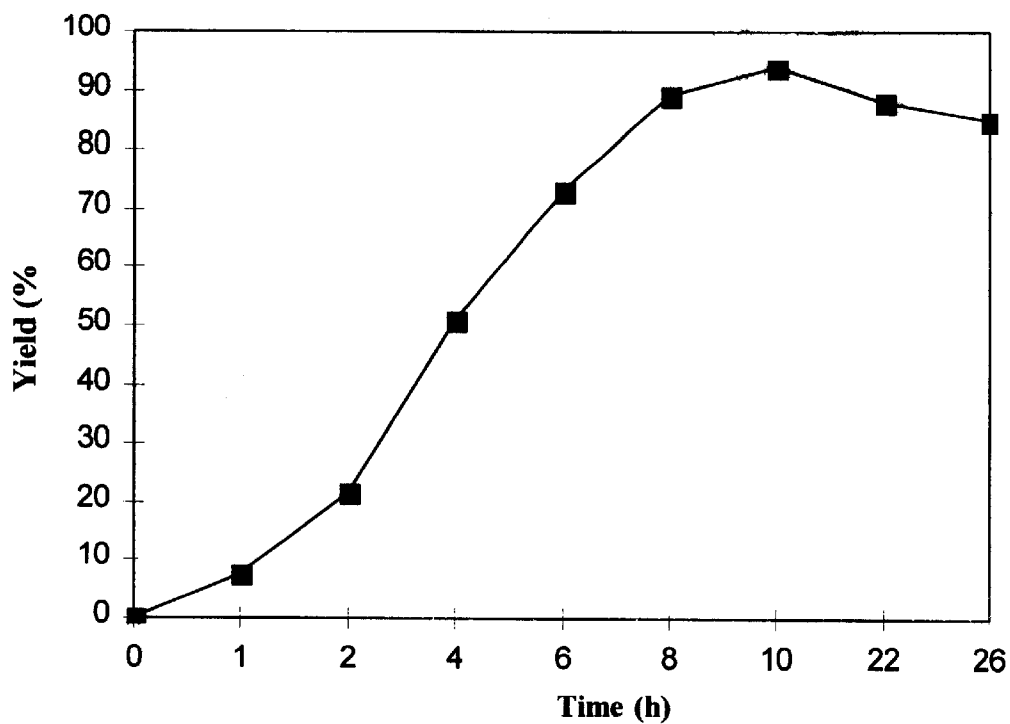
FIG. 1 shows the time dependent production of neotame via regioselective hydrolysis of 150 mM of neotame β-methyl ester by the lipase from Pseudomonas species type B in a buffer of 15% $CH_3CN$ and 250 mM Tris-Cl, pH 7.5 at room temperature.

This invention is directed to an improved method of preparing an N-alkylated aspartame derivative, namely N-[N-(3,3-dimethylbutyl)-L-α-aspartyl]-L-phenylalanine 1-methyl ester (neotame). This N-alkylated aspartame derivative is a highly potent sweetening agent.

This invention includes an alternative cost-effective strategy for preparing neotame via the enzymatic regioselective hydrolysis of neotame esters as shown in the following general reaction:

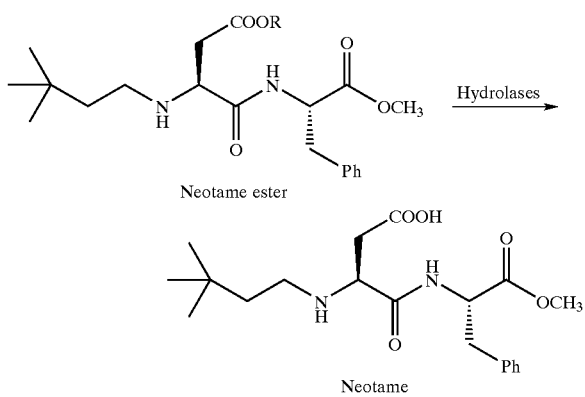

Neotame ester

Neotame

The neotame ester of the present invention is a compound of the formula:

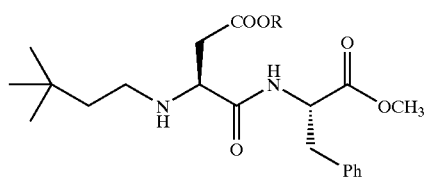

wherein R is alkyl, cycloalkyl, heterocycloalkyl, aryl or heteroaryl. Preferably, R is methyl, ethyl, propyl, isopropyl, t-butyl, isobutyl, cyclohexyl, benzyl or phenyl.

The neotame esters useful in the present invention can be synthesized according to the following general reaction scheme:

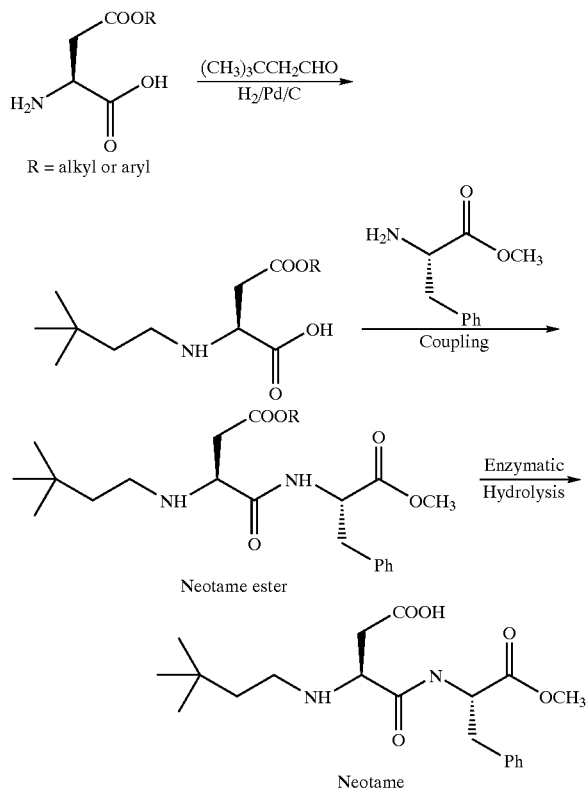

Neotame ester

Neotame

The starting materials of the above reaction, L-aspartic acid β-esters, are commercial available and can also be cost-effectively produced from regioselective hydrolysis of L-aspartic acid di-esters with pig liver esterase according to the method of U.S. Pat. No. 5,928,909. U.S. patent application Ser. No. 09/219,898, which has been allowed, discloses methods of synthesizing the t-butyl ester of neotame and N-neohexyl-L-aspartic acid B-t-butyl ester and is hereby incorporated by reference in its entirety herein. N-(3,3-d'imethylbutyl)-L-aspartic acid β-esters (N-neohexyl-L-aspartic acid β-esters ) may then be prepared by reductive alkylation of 3,3-dimethylbutyraldehyde with L-aspartic acid β-esters. The chemical coupling of N-(3,3-dimethylbutyl)-L-aspartic acid β-esters with L-phenylalanine methyl ester to form neotame esters can be accomplished through any of the following four strategies:

1. Synthesis of Neotame Esters Via Peptide Coupling Agents

There are many state of the art peptide coupling agents, including, without limitation, dicyclohexylcarbodiimide (DCC), diisopropylcarboduimide (DIPCDI), carbonyldiimidazole (CDI), 1-isobutyloxylcarbonyl-2-isobutyloxy-1,2-dihydroquinoline (IIDQ), benzotriazole-1-yl-oxyl-tri (dimethylamino)-phosphonium hexafluorophos phate (BOP), benzotriazole-1-yl-oxyl-tri-pyrrolidino-phosphonium hexafluorophosphate (PyBOP), bromo-tris-pyrrolidino-phosphonium hexafluorophosphate (PyBrOP), 2-(1H-benzotriazole-1-yl)-1,1,3,3-tetramethyluronium hexafluorophosphate (HBTU), 2-(1H-9-azabenzotriazole-1-yl)-1,1,3,3-tetramethyluronium hexafluorophosphate (HATU), 2-(5-norbomene-2,3-dicarboximido)-1,1,3,3-tetramethyluronium tetrafluoroborate (TNTU), O-(N-succinimidyl)-1,1,3,3-tetramethyluronium tetrafluoroborate (TSTU). However, these coupling reagents are extremely expensive for industrial scale production of peptide based sweeteners.

2. Synthesis of Neotame Esters Via Chloride of N-neohexyl-L-aspartic β-esters

The peptide amide bond of N-[N-(3,3-dimethylbutyl)-L-α-aspartyl β-ester]-L-phenylalaine 1-methyl ester can be formed via condensation of L-phenylalanine methyl ester with the acid chloride of N-(3,3-dimethylbutyl)-L-α-aspartic β-ester. The following reaction illustrates the preparation of N-(3,3-dimethylbutyl)-L-α-aspartic acid chloride β-ester:

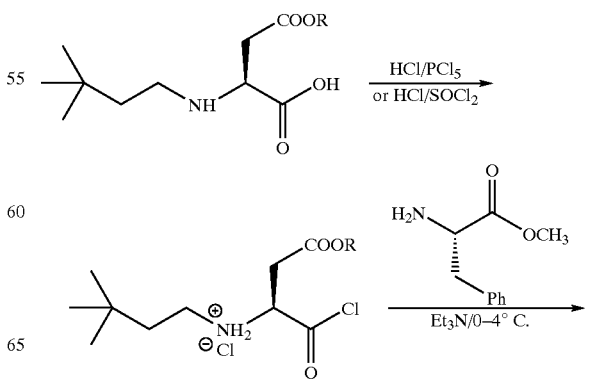

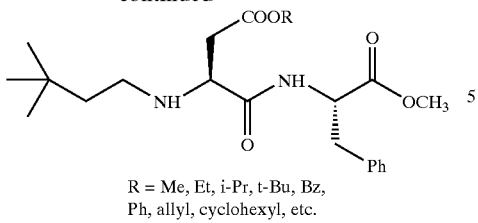

R = Me, Et, i-Pr, t-Bu, Bz, Ph, allyl, cyclohexyl, etc.

To avoid the possible intra molecular condensation of the second amine and the acid chloride, the N-neohexyl aspartic acid β-ester should be acidified with hydrochloride gas in inert solvents for a short period.

3. Synthesis of Neotame Esters Via N-neohexyl-L-aspartic β-ester Anhydride

Neotame esters may be prepared through a coupling of N-neohexyl-L-aspartic β-ester anhydride and L-phenylalanine methyl ester as follows:

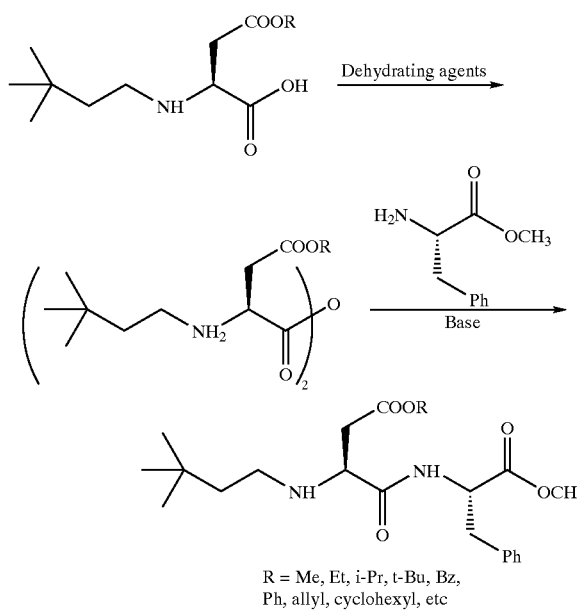

R = Me, Et, i-Pr, t-Bu, Bz, Ph, allyl, cyclohexyl, etc

The N-neohexyl-L-aspartic β-ester anhydride may be prepared by dehydration of two moles of N-neohexyl-L-aspartic acid β-esters using dehydrating agents. Exemplary dehydrating agents include phosphorus pentoxide, phosphorous trichloride, phosphoric acid, acid anhydrides, such as acetic anhydride and formic anhydride, carbodiimides, such as dicyclohexyl carbodiimide (DCC) and the like.

4. Synthesis of Neotame Esters Via N-neohexyl-L-aspartic β-ester Carboxy Anhydride Synthesis of neotame esters may also be accomplished through a coupling of N-neohexyl-L-aspartic β-ester carboxy anhydride and L-phenylalanine methyl ester as follows:

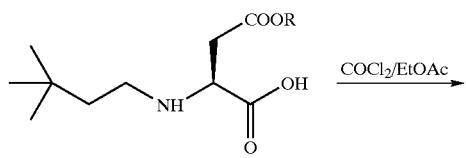

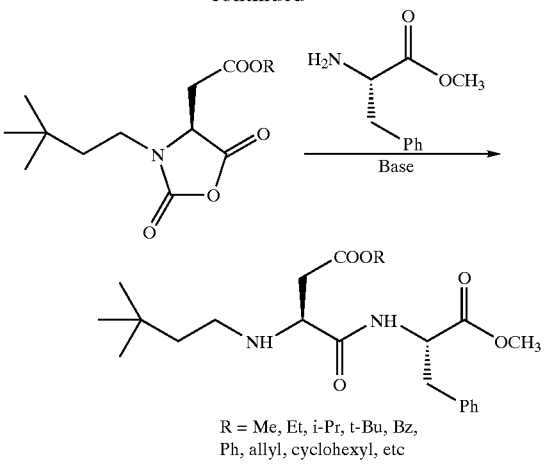

R = Me, Et, i-Pr, t-Bu, Bz, Ph, allyl, cyclohexyl, etc

The N-carboxy anhydride can be prepared by treatment of the β-ester with phosgene.

The neotame esters of the present invention include, but are not limited to, methyl, ethyl, propyl, allyl, isopropyl, t-butyl, isobutyl, cyclohexyl, benzyl and phenyl esters. The tert-butyl or benzyl esters achieve lower coupling yields than the other esters due to the instability of the esters in the strong acid conditions.

The present invention also includes the development of an effective method for the regioselective hydrolysis of neotame esters without effecting the peptide bond cleavage.

The present invention includes processes for the preparation of neotame through enzymatic regioselective hydrolysis of neotame ester using lipases or esterases from, for example, *Aspergillus niger, Aspergillus oryzae, Candida antarctica, Candida cylindracea, Candida lipolytica, Candida utilis*, hog pancreas, *Mucor javanicus, Mucor miehei, Penicillium roqueforti, Pseudomonas cepacia, Pseudomonas fluorescens, Rhizomucor miehei, Rhizopus arrhizus, Rhizopus delemer, Rhizopus niveus, Thermus aquaticus, Thermus flavus, Thermus thermophilus*, wheat germ, *Chromobacterium viscosum*, Pseudomonas sp., Pseudomonas sp. type B, Bacillus sp., *Bacillus stearothermophilus, Bacillus thermoglucosidasius, Electrophorus electricus*, porcine (hog) liver, horse liver, rabbit liver, *Saccharomyces cerevisiae, Thermoanerobium brockii*.

In a particularly preferred embodiment, the neotame ester is N-[N-(3,3-dimethylbutyl)-L-β-methyl ester-α-aspartyl]-L-phenylalanine 1-methyl ester of the formula:

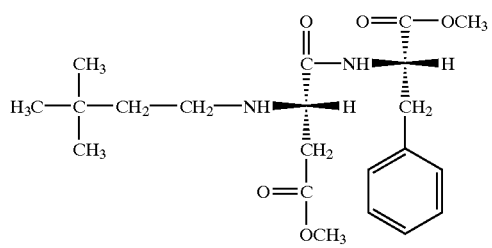

In particularly preferred embodiments of this invention, the hydrolases are lipases from Pseudomonas sp. type B or esterases from porcine liver.

The preparation of neotame esters, (N-[N-(3,3-dimethylbutyl)-L-β-ester-α-aspartyl]-L-phenylalanine 1-methyl ester, can be achieved via coupling of a derivate of the N-(3,3-dimethylbutyl)-L-β-ester-α-aspartic acid with L-phenylalanine methyl ester. The preferred methods of coupling are through N-(3,3-dimethylbutyl)-L-β-ester-α-aspartyl chloride, or N-neohexyl-L-β-ester aspartyl anhydride, or N-neohexyl-L-β-ester carboxy aspartyl anhydride.

To avoid the possible intra molecular condensation of the second amine and the acid chloride, the N-neohexyl aspartic acid N-ester is acidified with hydrochloride gas in inert solvents for a short period.

Lipases and esterases useful in the present invention were selected by screening using hydrolysis reactions which were conducted by mixing neotame esters (50 mM–300 mM) and a protein (0.095–10,000 U/ml) in 5%–50% either acetonitrile or DMSO or isopropanol or DMF or THF, buffered by 0.1 M–0.4 M either Tris—Cl, or NaH$_2$PO$_4$, or MES or Bis Tris propane, with a pH 5–8 at temperature 22° C. to 40° C. for approximately 2 to 48 hours. The results of the hydrolysis were evaluated by C18 column HPLC. A summary of the regioselective hydrolysis reactions with different lipases and esterases are provided in Table 1, Table 2 and Table 3.

TABLE 1

HPLC Analysis of the production of neotame via hydrolysis of neotame methyl ester by lipases and esterases at pH 7.5, 250 mM Tris-Cl with 150 mM neotame methyl ester, 20 mM CaCl$_2$, 15% CH$_3$CN, room temperature, 14h.

| No. | Sources of Lipases or Esterases | Specific activity in the mixture | Yields |
|---|---|---|---|
| 1 | Lipase from *Pseudomonas fluorescens* | 6180 U/ml | 2.15% |
| 2 | Lipase from *Penicillium roqueforti* | 0.755 U/ml | 1.76% |
| 3 | Lipase from *Mucor javanicus* | 0.0245 U/ml | 1.75% |
| 4* | Lipase from *Candida lipolytica* | 0.005 U/mg | 0.10% |
| 5* | Lipase from *Aspergillus oryzae* | 290 U/ml | 0.51% |
| 6 | Lipase from Pseudomonas species, type B | 690 U/ml | 92.45% |
| 7 | Lipase from Pseudomonas species | 10,160 U/ml | 2.53% |
| 8 | Lipase from *Chromobacterium viscosum* | 14,520 U/ml | 2.03% |
| 9* | Lipase from wheat germ | 0.40 U/ml | 1.34% |
| 10* | Lipase from *Rhizomucor miehei* | 2.55 U/ml | 2.27% |
| 11 | Lipase from *Pseudomonas cepacia* | 200 U/ml | 1.76% |
| 12* | Lipase from *Mucor miehei* | 6.5 U/ml | 0.45% |
| 13 | Lipase from *Candida cylindracea* | 12.0 U/ml | 1.73% |
| 14* | Lipase from *Candida antarctica* | 14.5 U/ml | 0.13% |
| 15* | Lipase from *Aspergillus niger* | 7.0 U/ml | 0.90% |
| 16 | Lipase from *Pseudomonas fluorescens* | 212.5 U/ml | 1.72% |
| 17 | Lipase from *Rhizopus arrhizus* | 0.010 U/ml | 1.71% |
| 18 | Lipase from *Rhizopus niveus* | 0.013 U/ml | 1.73% |
| 19* | Lipase from hog pancreas | 84.0 U/ml | 0.15% |
| 20* | Esterase from porcine liver (crude) | 100 U/ml | 28.46% |
| 21 | Esterase from porcine liver esterase (pure) | 350 U/ml | 58.71% |
| 22 | Esterase from rabbit liver | 40.0 U/ml | 13.50% |
| 23 | Esterase from *Thermoanaerobium brockii* | 0.020 U/ml | 1.28% |
| 24 | control | 0 | 0.05% |

*Peptide bonds were hydrolyzed as well.

Table 2. HPLC analysis of the production of neotame via hydrolysis of neotame methyl ester by lipases and esterases at pH 7.5, 250 mM Tris—Cl with 150 mM neotame methyl ester, 20 mM CaCl$_2$, 15% isopropanol, room temperature, 14h.

| No. | Sources of Lipases or Esterases | Specific activity in the mixture | Yields |
|---|---|---|---|
| 1 | Lipase from *Pseudomonas fluorescens* | 6180 U/ml | 2.49% |
| 2 | Lipase from *Penicillium roqueforti* | 0.755 U/ml | 1.91% |
| 3 | Lipase from *Mucor javanicus* | 0.0245 U/ml | 1.96% |
| 4* | Lipase from *Candida lipolytica* | 0.005 U/mg | 0.15% |
| 5* | Lipase from *Aspergillus oryzae* | 290 U/ml | 1.95% |
| 6 | Lipase from Pseudomonas species, type B | 690 U/ml | 78.60% |
| 7 | Lipase from Pseudomonas species | 4,060 U/ml | 2.47% |
| 8 | Lipase from *Chromobacterium viscosum* | 14,520 U/ml | 2.13% |
| 9* | Lipase from wheat germ | 0.40 U/ml | 1.47% |
| 10* | Lipase from *Rhizomucor miehei* | 2.55 U/ml | 2.33% |
| 11 | Lipase from *Pseudomonas cepacia* | 200 U/ml | 1.99% |
| 12* | Lipase from *Mucor miehei* | 6.5 U/ml | 0.50% |
| 13 | Lipase from *Candida cylindracea* | 12.0 U/ml | 1.91% |
| 14* | Lipase from *Candida antarctica* | 14.5 U/ml | 0.11% |
| 15* | Lipase from *Aspergillus niger* | 7.0 U/ml | 1.34% |
| 16 | Lipase from *Pseudomonas fluorescens* | 212.5 U/ml | 1.98% |
| 17 | Lipase from *Rhizopus arrhizus* | 0.010 U/ml | 1.86% |
| 18 | Lipase from *Rhizopus niveus* | 0.013 U/ml | 1.83% |
| 19* | Lipase from hog pancreas | 84.0 U/ml | 0.75% |
| 20* | Esterase from porcine liver (crude) | 100 U/ml | 20.65% |
| 21 | Esterase from porcine liver esterase (pure) | 350 U/ml | 65.28% |
| 22 | Esterase from rabbit liver | 40.0 U/ml | 13.72% |
| 23 | Esterase from *Thermoanaerobium brockii* | 0.020 U/ml | 1.19% |
| 24 | control | 0 | 0.10% |

*Peptide bonds were hydrolyzed as well.

Table 3. HPLC analysis of the production of neotame via hydrolysis of neotame methyl ester by lipases and esterases at pH 7.5, 250 mM TrisCl with 150 mM neotame methyl ester, 20 mM CaCl$_2$, 15% DMSO, 37° C., 8h.

| No. | Sources of Lipases or Esterases | Specific activity in the mixture | Yields |
|---|---|---|---|
| 1 | Lipase from *Pseudomonas fluorescens* | 6180 U/ml | 2.40% |
| 2 | Lipase from *Penicillium roqueforti* | 0.755 U/ml | 1.05% |
| 3 | Lipase from *Mucor javanicus* | 0.0245 U/ml | 0.62% |
| 4* | Lipase from *Candida lipolytica* | 0.005 U/mg | 0.63% |
| 5* | Lipase from *Aspergillus oryzae* | 290 U/ml | 0.085% |
| 6 | Lipase from Pseudomonas species, type B | 690 U/ml | 73.60% |
| 7 | Lipase from Pseudomonas species | 4,060 U/ml | 1.94% |
| 8 | Lipase from *Chromobacterium viscosum* | 14,520 U/ml | 2.22% |
| 9* | Lipase from wheat germ | 0.40 U/ml | 0.43% |
| 10* | Lipase from *Rhizomucor miehei* | 2.55 U/ml | 3.61% |
| 11 | Lipase from *Pseudomonas cepacia* | 200 U/ml | 1.28% |
| 12* | Lipase from *Mucor miehei* | 6.5 U/ml | 0.45% |
| 13 | Lipase from *Candida cylindracea* | 12.0 U/ml | 1.04% |
| 14* | Lipase from *Candida antarctica* | 14.5 U/ml | 0.88% |
| 15* | Lipase from *Aspergillus niger* | 7.0 U/ml | 1.29% |
| 16 | Lipase from *Pseudomonas fluorescens* | 212.5 U/ml | 1.04% |
| 17 | Lipase from *Rhizopus arrhizus* | 0.010 U/ml | 1.18% |
| 18 | Lipase from *Rhizopus niveus* | 0.013 U/ml | 0.59% |
| 19* | Lipase from hog pancreas | 84.0 U/ml | 0.52% |
| 20* | Esterase from porcine liver (crude) | 100 U/ml | 35.91% |
| 21 | Esterase from porcine liver esterase (pure) | 350 U/ml | 64.95% |
| 22 | Esterase from rabbit liver | 40.0 U/ml | 10.25% |

| No. | Sources of Lipases or Esterases | Specific activity in the mixture | Yields |
|---|---|---|---|
| 23 | Esterase from *Thermoanaerobium brockii* | 0.020 U/ml | 1.14% |
| 24 | control | 0 | 0.57% |

*Peptide bonds were hydrolyzed as well.

Figure 2:
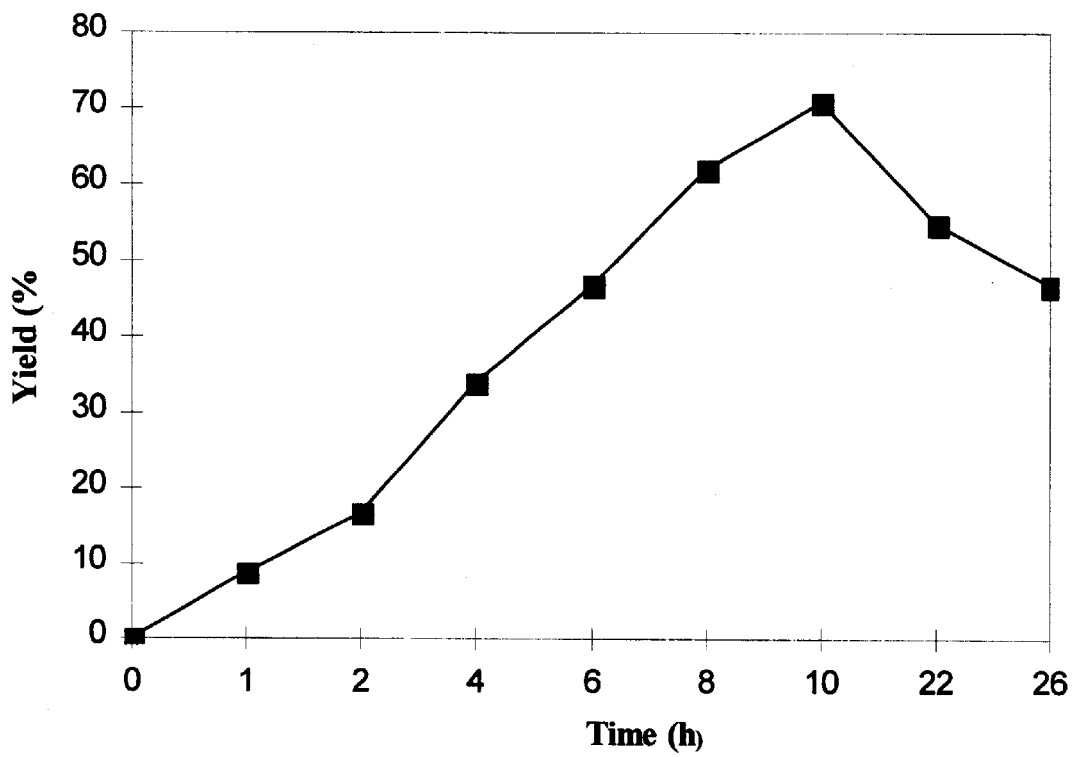
FIG. 2 shows the time dependent production of neotame via regioselective hydrolysis of 150 mM of neotame β-methyl ester by the esterase from porcine liver in a buffer of 15% $CH_3CN$ and 250 mM Tris-Cl, pH 7.5 at room temperature.
Figure 3:
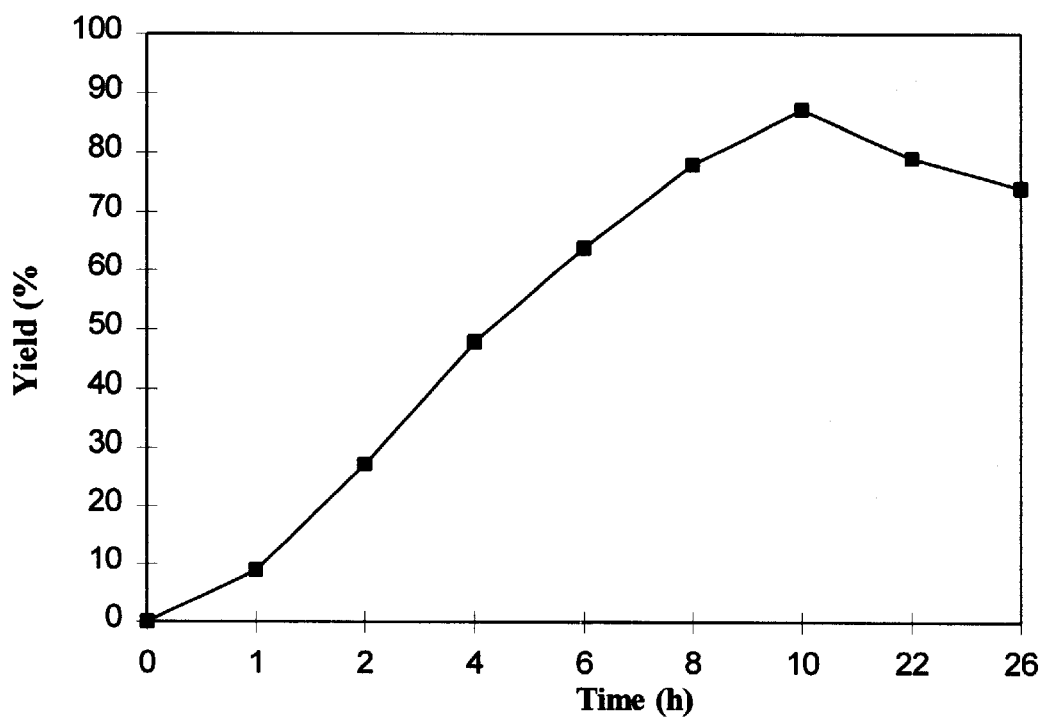
FIG. 3 shows the time dependent production of neotame via regioselective hydrolysis of 150 mM of neotame β-methyl ester by the lipase from Pseudomonas species type B in a buffer of 15% DMSO and 250 mM Tris-Cl, pH 7.5 at room temperature.
Figure 4:
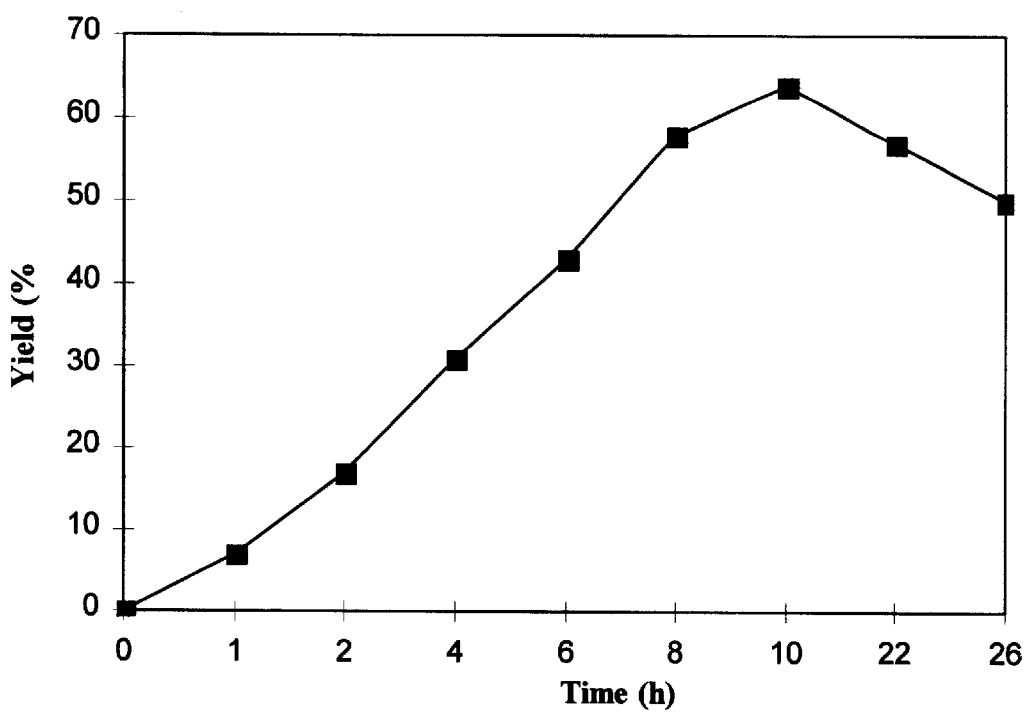
FIG. 4 shows the time dependent production of neotame via regioselective hydrolysis of 150 mM of neotame β-methyl ester by the esterase from porcine liver in a buffer of 15% DMSO and 250 mM Tris-Cl, pH 7.5 at room temperature.

Low yields often resulted from the fact that the commercial hydrolases used were not pure, and some preparations showed protease activities such as the cleavage of the dipeptide bond to form neohexyl aspartic acid and L-phenylalanine methyl ester. These proteolytic properties contributed to the poor selective hydrolysis evident with some enzymes as demonstrated in Tables 1 to 3. A lipase from Pseudomonas species type B (No. 6 in Tables 1–3) and an esterase from porcine liver (No. 21 in Tables 1–3) provide high hydrolysis yields (approximately 65%–95%) within 15 hours as shown in FIGS. 1 to 4. Other enzymes and purified forms of the enzymes listed in Tables 1–3 may provide substantially improved yields and are included in this invention.

Several factors affecting catalytic performance of these lipases and esterases were investigated. Organic solvents, pH value, concentration of the buffer, and temperature have significant effects on enzyme activity but have little effect on enzyme selectivity.

Preferably, 5%–50% organic solvents, including acetonitrile, dimethyl sulfoxide (DMSO), tetrahydrofuran, acetone, dimethyl formamide (DMF), dioxane, isopropanol, ethanol, methanol, or the like, should be present in the reaction mixture to help solubilize the neotame ester and accelerate the hydrolysis. However, over 50% of the organic co-solvents, in particular, over 50% of methanol, ethanol and isopropanol in the hydrolysis mixture can reduce the hydrolysis rate due to the denaturation of the enzymes.

All methods described herein may be performed in the presence of a suitable buffer. The buffer may be selected from the group comprising 10 mM–500 mM of phosphate, acetate, Tris, MES, MES and Bis Tris Propane at pH 4–10, preferably at pH 5.5–8.0.

The enzymatic hydrolysis reaction can be conducted at 20° C.–60° C. The hydrolysis rate is increased with temperature increase. But selectivity is slightly decreased with temperature increase. In a preferred embodiment of the present invention, the temperature is 20° C. to 40° C.

Empirical observation has shown that metal ion cofactors (such as $Ca^{2+}$, $Mg^{2+}$, $Zn^{2+}$) have little effect on the hydrolase selectivity and do not significantly increase the hydrolase activities.

A further advantage of the present invention is that the lipases and esterases may be immobilized on clay, silica gel, Celite, DEAE-Sephadex, or CM-Sephadex, or other similar supports in order to facilitate the recycling of the enzymes and therefore accelerate the production of neotame. The enzymatic hydrolysis can be accomplished in a batch system as well as in a fluidized bed column. Hydrolases may be recombinant enzymes which are cloned and expressed in *E. Coli*, yeast or other suitable hosts known in the art.

The examples below are provided in order to impart a better understanding of the present invention; however, one skilled in the art will readily appreciate that the specific methods and results discussed are merely illustrative of the invention and no limitation of the invention is implied.

EXAMPLE 1

General screening of the lipases and the esterases for production of neotame via hydrolysis of neotame esters In a typical experiment, a lipase or an esterase from, for example, *Aspergillus niger*, *Aspergillus oryzae*, *Candida antarctica*, *Candida cylindracea*, *Candida lipolytica*, *Candida utilis*, hog pancreas, *Mucor javanicus*, *Mucor miehei*, *Penicillium roqueforti*, *Pseudomonas cepacia*, *Pseudomonas fluorescens*, *Rhizomucor miehei*, *Rhizopus arrhizus*, *Rhizopus delemer*, *Rhizopus niveus*, *Thermus aquaticus*, *Thermus flavus*, *Thermus thermophilus*, wheat germ, *Chromobacterium viscosum*, Pseudomonas sp., Pseudomonas sp. type B, etc. Bacillus sp., *Bacillus stearothermophilus*, *Bacillus thermoglucosidasius*, *Electrophorus electricus*, hog liver, horse liver, rabbit liver, *Saccharomyces cerevisiae*, *Thermoanaerobium brockii*, or the like (Fluka Chemical Company, Milwaukee, Wis.; and Sigma, St. Louis, Mo., USA) was added to a suspension of neotame esters (0.05 M–0.3 M, its synthesis is shown in Example 2) in a mixture of 5%–25% of acetonitrile or 5%–25% of DMSO or 5%–15% isopropanol with a buffer of 0.05 M–0.4 M phosphate, or Tris—Cl, or MES, or Bis Tris Propane, or Acetate at pH 5.5–8.0 buffer at room temperature to 40° C. in centrifuge tubes. After shaking for 4 hours to 48 hours, two times amount methanol or DMSO was added to the reaction mixture. The denatured protein was spun down, and the supernatant was subjected to C-18 column HPLC for hydrolysis analysis. Exemplary results are presented in Table 1, Table 2 and Table 3. The neotame product can be isolated either by crystallization from methanol/water, ethanol/hexane or by silica gel chromatography (HOAc/$CH_3OH/CHCl_3$ 0.1:1:7).

EXAMPLE 2

General Preparation of Neotame Via the Hydrolysis of Neotame Methyl Ester With a Lipase (1) Synthesis of N-(3,3-Dimethylbutyl)-L-aspartic acid β-Methyl Ester To a Parr bottle containing a solution of L-aspartic acid β-methyl ester (10 g, 54.4 mmol), triethyl amine (8 ml), 3,3-dimethylbutyraldehyde (5.5 g, 55.0 mmol) and methanol (80 ml) was added 0.75 g of Pd/C (4% palladium on carbon, 50% wet). After stirring for 30 minutes, the mixture was hydrogenated at 50 psi/room temperature for 8 hours. The mixture was filtered through a Celite bed, and the bed was washed with methanol (50 ml) and water (50 ml). The filtrate and washings were combined and concentrated. The pH of the aqueous solution (50 ml) was adjusted to pH 3 with concentrated hydrochloric acid, followed by extraction with chloroform (20 ml). The remaining aqueous solution was concentrated, and the crude product was crystallized from water/acetone to afford 8.6 g (72%) of the N-(3,3-dimethylbutyl)-L-aspartic acid β-methyl ester. $^1$H NMR ($D_2O$), 3.80 (t, 1H, J=5.6+5.8 Hz), 3.59 (s, 3H), 2.97 (dd, 2H, J=7.8, 14.0 Hz), 2.89 (d, 2H, J=5.6 Hz), 1.47 (m, 2H), 0.77 (s, 9H); $^{13}$C NMR 172.62, 172.46, 58.19, 53.07, 44.65, 39.14, 34.20, 29.26, 28.53.

(2) Synthesis of Neotame Methyl Ester Via N-neohexyl-L-aspartic Acid Chloride

A rapid stream of hydrogen chloride (dried through a concentrated sulfuric acid) was bubbled through (ca. 5 bubbles/sec) a stirred suspension of N-neohexyl-L-aspartic acid β-methyl ester (5.0 g, 19.6 mmol) in 80 ml of anhydrous chloroform, at 0–4° C., for 15 minutes. Finely powdered phosphorus pentachloride (4.08 g, 19.57 mmol) was then added, and the reaction was kept at 0–10° C. for 4–5 hours. The solvent was evaporated, and the mixture was dried on an oil pump for 45 minutes. The acid chloride obtained was re-dissolved in anhydrous dichloromethane or chloroform and used directly for next step without further purification.

To a solution of L-phenylalaine methyl ester (4.5 g, 20.86 mmole) in anhydrous triethylamine (10 ml) and anhydrous dichloromethane (30 ml) at 0–4° C. was added dropwise the crude N-neohexyl-L-aspartic acid chloride (generated from 4.0 g of N-neohexyl-L-aspartic acid 0-methyl ester) in 10 ml anhydrous dichloromethane. The reaction was stirred at 0–10° C. for 6 hours, and the solvent was evaporated. The remaining oil was re-dissolved in chloroform (100 ml) and washed with 100 ml of 0.2 M $NaH_2PO_4$, pH 3.0 and 100 ml of $H_2O$. The organic phase was dried with anhydrous $MgSO_4$, filtered, evaporated and passed through a short silica gel column using 45% ethyl acetate in hexane as an eluant. The neotame β-methyl ester was eluted out and evaporated to an oil (6.01 g, 79% from neohexyl aspartic acid β-methyl ester). $R_f$=0.46 (1:1 EtOAc/Hexane), $^1H$ NMR ($CDCl_3$) 7.80 (d, 1 H, J=8.1 Hz), 7.28 (m, 3H), 7.13 (m, 2H), 4.83 (dd, 1H, J=6.1, 14.6 Hz), 3.70 (s, 3H), 3.67 (s, 3H), 3.40 (dd, 1H, J=4.0, 8.1 Hz), 3.11 (m, 2H), 2.70 (dd, 1H, J=4.0, 16.0 Hz), 2.51 (m, 3H), 1.30 (m, 2H), 0.85 (s, 9H); $^{13}C$ NMR ($CDCl_3$) 172.11, 171.72, 135.94, 129.24, 128.53, 127.08, 59.14, 52.69, 52.23, 51.89, 44.45, 44.00, 37.98, 35.93, 29.75, 29.51.

(3) Preparation of Neotame Via the Hydrolysis of Neotame Methyl Ester With a Lipase In a typical experiment, a lipase from Pseudomonas sp. type B (139 Units/mg, 50 mg, Fluka Chemical Company, Milwaukee, Wis., USA) was added to a suspension of neotame methyl ester (5.01 g, 12.75 mmol) in a mixture of 10 ml of acetonitrile and 65 ml of 0.05 M sodium phosphate, pH 7.0 buffer at room temperature. The pH was kept at 7.0 by addition of 0.1 M NaOH with an automatic pH titrator (Brinkman, Westbury, N.Y.). After hydrolysis was complete, confirmed by HPLC (about 8–12 hours with yield of about 80%–95%), the mixture was carefully acidified with 0.1 M HCl to pH 3.0. The product was extracted with ethyl acetate (5×50 ml). The organic phase was dried over anhydrous magnesium sulfate and evaporated under reduced pressure. The subject compound was crystallized from ethanol/hexane at 4° C. to give 2.90 g (61%) of neotame. The remaining mother liquid was concentrated and subjected to silica gel chromatographic purification (1:7 $CH_3OH/CHCl_3$) to obtain 0.86 g (18%) of additional neotame.

EXAMPLE 3

Preparation of Neotame Via the Hydrolysis of Neotame Methyl Ester With an Esterase In a typical experiment, an esterase from porcine liver (5,340 Units, Sigma, St. Louis, Mo., USA) was added to a suspension of neotame methyl ester (2.19 g, 5.58 mmol) in a mixture of 6 ml of acetonitrile and 30 ml of 0.05 M sodium phosphate, pH 7.0 buffer at room temperature. The pH was kept at 7.0 by addition of 0.1 M NaOH with an automatic pH titrator (Brinkman, Westbury, N.Y.). After hydrolysis was complete, as confirmed by HPLC (about 10 hours with yields around 75%–90%), the mixture was carefully acidified with 0.1 M HCl to pH 3.0. The product was extracted with ethyl acetate (5×50 ml). The organic phase was dried over anhydrous magnesium sulfate and evaporated under reduced pressure. The crude compound was subjected to silica gel chromatographic purification (1:7 $CH_3OH/CHCl_3$) and crystallized from ethanol/hexane at 4° C. to give 1.28 g (60%) neotame.

EXAMPLE 4

Preparation of Neotame Via the Hydrolysis of Neotame Methyl Ester With a Lipase

In a typical experiment, a lipase from Pseudomonas sp. type B (139 Units/mg, 25 mg, Fluka Chemical Company, Milwaukee, Wis., USA) was added to a suspension of neotame methyl ester (2.00 g, 5.48 mmol) in a mixture of 3 ml of DMSO and 10 ml of 20 mM $CaCl_2$ at room temperature. The pH value was kept at 7.0 by addition of 0.1 M NaOH with an automatic pH titrator (Brinkman, Westbury, N.Y.). After hydrolysis was complete, confirmed by HPLC (about 10 hours with yields around 75%–90%), the mixture was carefully acidified with 0.1 M HCl to pH 3.0. The product was extracted with ethyl acetate (5×50 ml). The organic phase was dried over anhydrous magnesium sulfate and evaporated under reduced pressure. The crude compound was subjected to silica gel chromatographic purification (1:7 $CH_3OH/CHCl_3$) and crystallized from ethanol/hexane at 4° C. to give 1.22 g (58%) neotame.

EXAMPLE 5

Preparation of Neotame Via the Enzymatic Hydrolysis of Neotame β-t-butyl Ester (1) Synthesis of N-(3,3-dimethylbutyl)-L-aspartic acid β-t-butyl Ester To a Parr bottle containing a solution of L-aspartic acid β-t-butyl ester (10.0 g, 52.85 mmol), triethyl amine (8 ml), 3,3-dimethylbutyraldehyde (5.31 g, 53.0 mmol) and methanol (80 ml) were added to 0.75 g of Pd/C (4% palladium on carbon, 50% wet). After stirring for 30 minutes, the mixture was hydrogenated at 50 psi/room temperature for 8 hours. The mixture was filtered through a Celite bed, and the bed was washed with methanol (50 ml) and water (50 ml). The filtrate and washings were combined and concentrated. The aqueous solution was extracted with chloroform (20 ml) followed by adjustment to pH 3 with 0.1 M hydrochloric acid. The solid precipitate was filtered and crystallized from methanol/water to afford 10.1 g (70%) of the N-(3,3-Dimethylbutyl)-L-aspartic acid β-t-butyl ester. $^1H$ NMR ($CDCl_3$), 3.57 (dd, 1H, J=3.8, 9.3 Hz), 2.89–2.75 (m, 3H), 2.60 (dd, 1H, J=9.3, 17.0 Hz), 1.58 (m, 2H), 1.47 (m, 9H), 0.90 (s, 9H); $^{13}C$ NMR 172.33, 169.48, 83.65, 57.57, 44.12, 41.68, 35.43, 29.81, 29.29, 27.91.

(2) Synthesis of Neotame β-t-butyl Ester Via a Peptide Coupling Agent

A solution of N-(3,3-dimethylbutyl)-L-aspartic acid β-t-butyl ester (4.0 g, 14.65 mmol), L-phenylalanine methyl ester (3.2 g, 14.83 mmol) and triethylamine (2.8 ml, 20 mmol) in dichloromethane (100 ml) was stirred while benzotriazole-1-yl-oxyl-tri(dimethylamino)-phosphonium hexafluorophosphate (BOP, 6.48 g, 14.65 mmol) was added. Stirring was continued at room temperature for 2 hours. A saturated sodium chloride solution (200 ml) was added and the product extracted with ethyl acetate (3×50 ml). The combined extracts were washed with 0.1 M $NaH_2PO_4$ pH 3.0, 10% $NaHCO_3$ solution and water. The dried (MgSO4) solution was evaporated in vacuo, and the crude product was subjected to silica gel chromatographic purification to obtained 5.1 g (81%) of neotame β-t-butyl ester. $R_f$=0.65 (1:1 EtOAc/Hexane), $^1H$ NMR ($CDCl_3$) 7.78 (d, 1H, J=8.3 Hz), 7.20 (m, 3H), 7.06 (d, 2H, J=7.6 Hz), 4.77 (m, 1H,), 3.63 (s, 3H), 3.31 (dd, 1H, J=4.0, 8.1 Hz), 3.04 (m, 2H), 2.60 (dd, 1H, J=4.0, 16.1 Hz), 2.46 (m, 2H), 2.30 (dd, 1H, J=9.0, 16.0 Hz), 1.37 (s, 3H), ), 1.25 (t, 2H, J=8.3+8.1 Hz), 0.79 (s, 3H); $^{13}C$ NMR ($CDCl_3$) 1.71.68, 170.83, 135.94, 129.22, 128.50, 127.03, 81.27, 59.49, 52.67, 52.18, 44.55, 43.97, 37.92, 37.72, 29.72, 29.47, 28.00.

(3) Synthesis of Neotame β-t-butyl Ester Via N-neohexyl-L-aspartic Acid Chloride A rapid stream of hydrogen chloride (dried using concentrated sulfuric acid) was bubbled through (ca. 5 bubbles/sec)

a stirred suspension of N-neohexyl-L-aspartic acid β-t-butyl ester (2.5 g, 9.15 mmol) in 60 ml of anhydrous chloroform at 0–4° C. for 5 minutes. Finely powdered phosphorus pentachloride (1.91 g, 9.15 mmole) was then added, and the reaction was kept at 0–10° C. for 4 hours. The solvent was evaporated, and the mixture was dried with oil pump for 1 hours. The acid chloride obtained was re-dissolved in anhydrous dichloromethane and used directly for next step without further purification.

To a solution of L-phenylalaine methyl ester (2.0 g, 9.27 mmol) in anhydrous triethylamine (10 ml) and anhydrous dichloromethane (20 ml) at 0–4° C. was added dropwise the crude N-neohexyl-L-aspartic acid chloride (generated from 4.0 g of N-neohexyl-L-aspartic acid β-t-butyl ester) in 10 ml anhydrous dichloromethane. The reaction was kept at 0–10° C. for 6 hours and the solvent was evaporated. The remaining oil was re-dissolved in chloroform (100 ml), washed with 100 ml of 0.2 M NaH$_2$PO$_4$, pH 3.0 and 100 ml of H$_2$O. The organic phase was dried with anhydrous MgSO$_4$, filtered, evaporated and run through a short silica column with 35% ethyl acetate in hexane. The neotame β-t-butyl ester was eluted out and evaporated to oil (1.25 g, 31% from neohexyl aspartic acid β-t-butyl ester).

(4) Preparation of Neotame Via the Hydrolysis of Neotame β-t-butyl Ester With a Lipase In a typical experiment, a lipase from Pseudomonas sp. type B (139 Units/mg, 35 mg, Fluka Chemical Company, Milwaukee, Wis., USA) was added to a suspension of neotame β-t-butyl ester (2.07 g, 4.76mmol) in a mixture of 5 ml of acetonitrile and 25 ml of 0.02 M sodium phosphate, 0.01 M CaCl$_2$, pH 7.0 buffer at room temperature. The pH was kept at 7.0 by addition of 0.1 M NaOH with an automatic pH titrator (Brinkman, Westbury, N.Y.). After hydrolysis was complete, confirmed by HPLC (about 8 hours), the mixture was carefully acidified with 0.1 M HCl to pH 3.0. The product was extracted with ethyl acetate (4×40 ml). The organic phase was dried over anhydrous magnesium sulfate and evaporated under reduced pressure. The crude compound was subjected to chromatographic purification (1:7 CH$_3$OH/CHCl$_3$) and crystallized with ethanol/hexane to give 0.60 g (33%) of neotame.

EXAMPLE 6

Preparation of Neotame Via the Hydrolysis of Neotame β-t-butyl Ester With an Esterase In a typical experiment, an esterase from porcine liver (5340 Units, Sigma, St. Louis, Mo., USA) was added to a suspension of neotame β-t-butyl ester (2.01 g, 4.63 mmol) in a mixture of 5 ml of acetonitrile and 25 ml of 0.05 M sodium phosphate, pH 7.0 buffer at room temperature. The pH was kept at 7.0 by addition of 0.1 M NaOH with an automatic pH titrator Brinkman, Westbury, N.Y. After hydrolysis was complete, confirmed by HPLC (about 10 hours with yield of 45%), the mixture was carefully acidified with 0.1 M HCl to pH 3.0. The product was extracted with ethyl acetate (5×50 ml). The organic phase was dried over anhydrous magnesium sulfate and evaporated under reduced pressure. The crude compound was subjected to chromatographic purification (1:7 CH$_3$OH/CHCl$_3$) and crystallized from ethanol/hexane at 4° C. to give 0.51 g (29%) of neotame.

We claim:

1. A process for producing neotame comprising the steps of:

contacting a neotame ester having the formula

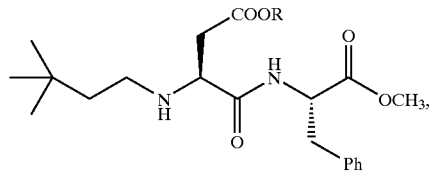

wherein R is selected from the group consisting of methyl, ethyl, propyl, isopropyl, butyl and isobutyl, with an enzyme selected from the group consisting of a lipase obtained from a Pseudomonas sp. Type B source and an esterase obtained from a porcine liver source to regioselective hydrolyse the neotame ester; and isolating neotame.

2. The process according to claim 1, wherein the neotame ester is N-[N-(3,3-dimethylbutyl)-L-β-methyl ester-α-aspartyl]-L-phenylalanine 1-methyl ester.

3. The process according to claim 1 further comprising the step of producing the neotame ester by a chemical or an enzymatic method prior to the hydrolysing step.

4. The process according to claim 3, wherein the neotame ester is produced via peptide coupling agents.

5. The process according to claim 3, wherein the neotame ester is produced via chloride of N-neohexyl-L-aspartic β-esters.

6. The process according to claim 3, wherein the neotame ester is produced via N-neohexyl-L-aspartic β-esters anhydride.

7. The process according to claim 3, wherein the neotame ester is produced via N-neohexyl-L-aspartic β-ester carboxy anhydride.

* * * * *